United States Patent [19]
Fitch et al.

[11] Patent Number: 5,626,859
[45] Date of Patent: May 6, 1997

[54] ECTOPARASITE CONTROL STICK FOR DOMESTICATED ANIMALS

[76] Inventors: Joanne A. Fitch; Kanta Kumar; Duane M. Pinault, all of P.O. Box 33427, St. Paul, Minn. 55133-3427

[21] Appl. No.: 438,648

[22] Filed: May 10, 1995

Related U.S. Application Data

[63] Continuation of Ser. No. 176,535, Dec. 30, 1993, abandoned.

[51] Int. Cl.$^6$ ............................................. A01N 25/08
[52] U.S. Cl. .................. 424/409; 424/405; 424/407; 424/DIG. 5; 424/DIG. 10; 574/919
[58] Field of Search .............. 43/124, 131; 119/156, 119/157, 861; 514/919, 65–74, 521–557, 570, 571; 523/122; 525/5; 424/78.03, 78.18, 772.1, 772.4, 785, 405, 407–409

[56] References Cited

U.S. PATENT DOCUMENTS

| | | |
|---|---|---|
| 2,465,470 | 3/1949 | Omonunchro et al. ............... 167/42 |
| 2,818,167 | 12/1957 | McKinley ................... 206/56 |
| 2,819,995 | 1/1958 | Wassell ................... 167/42 |
| 3,162,575 | 12/1964 | Lang ................... 167/53.2 |
| 3,590,118 | 6/1971 | Conrady ................... 424/19 |
| 3,629,392 | 12/1971 | Banker et al. ................... 424/22 |
| 3,826,232 | 7/1974 | Duffey et al. ................... 119/157 |
| 4,146,619 | 3/1979 | Lover et al. ................... 424/184 |
| 4,473,582 | 9/1984 | Greene ................... 424/305 |
| 4,762,718 | 8/1988 | Marks, Sr. ................... 424/409 |
| 4,816,256 | 3/1989 | Randen ................... 424/405 |
| 4,972,037 | 11/1990 | Garbe et al. ................... 526/245 |
| 4,981,902 | 1/1991 | Mitra et al. ................... 524/547 |
| 4,981,903 | 1/1991 | Garbe et al. ................... 524/547 |
| 5,032,460 | 7/1991 | Kantner et al. ................... 428/449 |
| 5,194,265 | 3/1993 | Boettcher et al. ................... 424/411 |
| 5,206,022 | 4/1993 | Nichols ................... 424/409 |
| 5,292,504 | 3/1994 | Cardin et al. ................... 424/70 |
| 5,294,445 | 3/1994 | Sieveking et al. ................... 424/411 |

FOREIGN PATENT DOCUMENTS

| | | |
|---|---|---|
| 1286985 | 7/1991 | Canada . |
| 0135853A2 | 4/1985 | European Pat. Off. . |
| 0251464 | 1/1988 | European Pat. Off. . |
| 0251464A3 | 1/1988 | European Pat. Off. . |
| 2150437 | 7/1985 | United Kingdom . |
| WO93/23009 | 11/1993 | WIPO . |

OTHER PUBLICATIONS

U.S. Application Serial No. 08/033,702, Kumar at al., filed Mar. 16, 1993, titled "Poly(fluoroaliphatic)/Vinyl Grafted Polyorganosiloxane Copolymers as Fabric Protectors".

U.S. Application Serial No. 08/087,959, Matteson et al., filed Jul. 6, 1993, titled "Substantive Insect Repellent/Toxicant Composition".

U.S. Application Serial No. 08/259,931, Kumar et al., filed Jun. 13, 1994, titled "A Method of Making Poly(fluoroaliphatic)/Vinyl Grafted Organopolysiloxane Copolymers, The Copolymers Made Thereby, and Surface Coating Compositions Comprising the Copolymers".

*Primary Examiner*—Neil S. Levy
*Attorney, Agent, or Firm*—Gary L. Griswold; Walter N. Kirn; Paul W. Busse

[57] ABSTRACT

The present disclosure describes an solid ectoparasite control composition for topical application to the hair coat or fur of a domesticated animal or household pet, such as a dog or cat, to control ectoparasites. The disclosure also describes an applicator package for applying an ectoparasite control composition that is in the form of a molded stick, by rubbing or spreading it on the hair coat of the animal. Methods of making and applying solid ectoparasite control compositions are also described in the present disclosure.

4 Claims, 1 Drawing Sheet

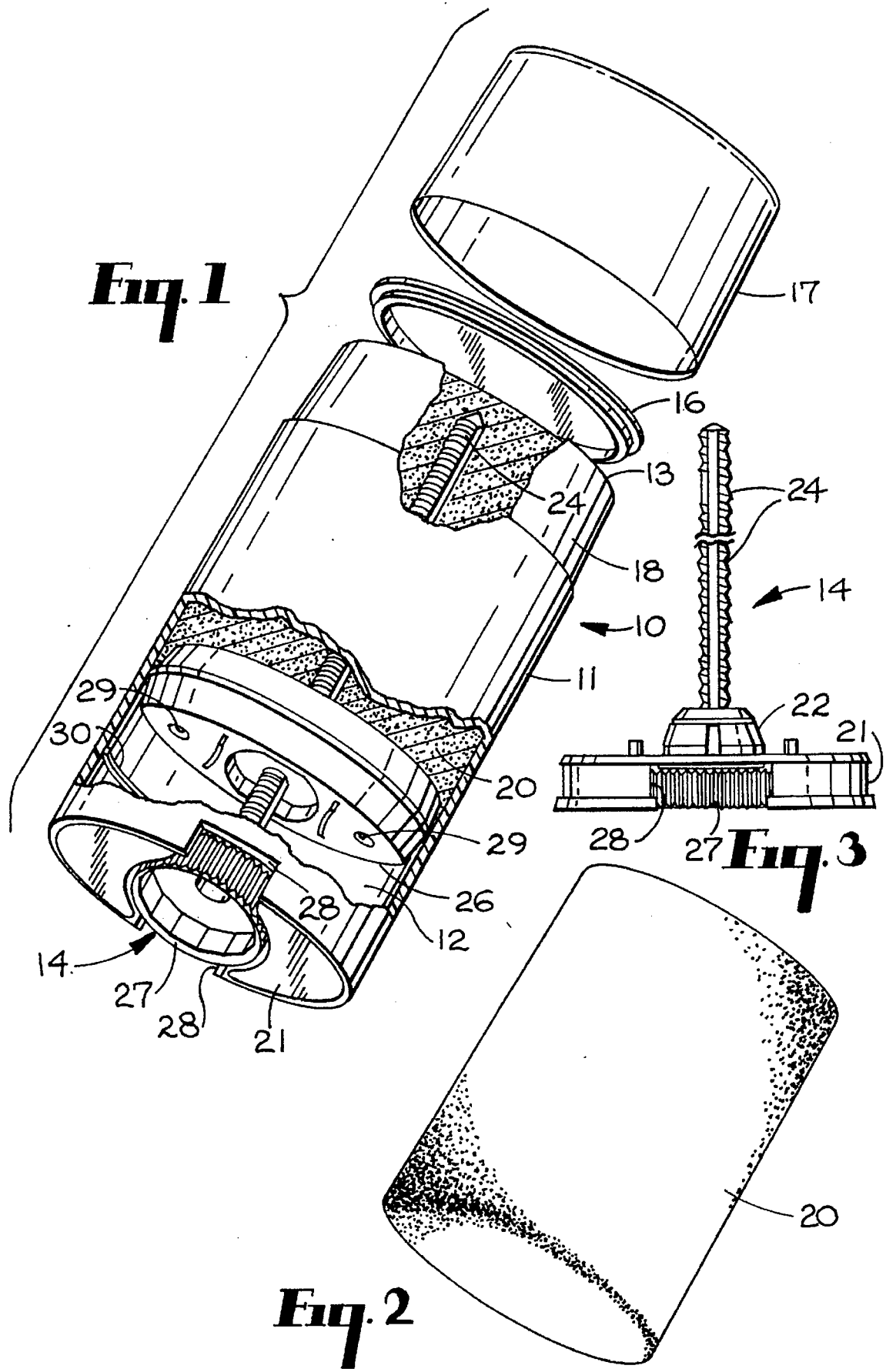

ECTOPARASITE CONTROL STICK FOR DOMESTICATED ANIMALS

This is a continuation of application Ser. No. 08/176,535 filed Dec. 30, 1993, now abandoned.

This invention relates to an ectoparasite control composition for topical application to the hair coat or fur of a domesticated animal or household pet, such as a dog or cat, to control ectoparasites, such as fleas or ticks. In another aspect, the invention relates to an applicator package for applying an ectoparasite control composition, in the form of a molded stick, by rubbing or spreading it on the hair coat of such animal and thereby coating it with the composition. In further aspects, the invention relates to a method of making ectoparasite control compositions and to a method of applying the same.

Man is constantly at war with harmful pests that annoy, bite, and cause infections. Various compositions and application techniques are known for controlling or eliminating biting or blood-sucking pests (ectoparasites), such as fleas, ticks, flies, and lice, which often irritate or infest animals. Of particular concern is the presence and effect of such pests on household pets or companion animals, such as dogs and cats, and other domesticated animals, such as horses. "Fleas are big trouble—and big business," according to *The Wall Street Journal*, Dec. 28, 1993, page A1, and Americans spend one billion dollars a year on various products to kill a species of fleas that preys on both dogs and cats.

Over the years a host of aerosols and space sprays, liquids, soaps, shampoos, wettable powders, granules, baits, and dusts, as well as various devices or articles, such as insecticidal ear tags, tail tags, collars, strips, and applicators that contain push-up insecticide stick formulations, have been proposed, used, or described in the patent literature for the control of pests.

A recent patented composition for control of insects is the insect repellent/toxicant composition described in Canadian Patent 1,286,985 (Matteson et al.), the composition being substantive to animal hide and hair and comprising a pyrethroid insecticide, a certain water-insoluble acrylate polymer, and a liquid carrier.

A number of patents describe insect repellents or insecticides in the form of a stick. U.S. Pat. No. 3,162,575 (Lang) describes controlling face flies on livestock by applying to the animal's face a composition, preferably in the form of a stick, that includes an insecticide, microcrystalline wax, and an oil. U.S. Pat. No. 3,826,232 (Duffey et al.) describes a pest control stick formulation that can be applied to the neck or face of domesticated animals to eliminate and control pests in general and fleas in particular on dogs and cats, the stick being dispensed from a tubular receptacle and comprising a certain carbamate as the active ingredient and, as a bodying or carrying agent, a polyethylene glycol or derivative, the stick formulation also including fatty acid such as stearic acid, and fatty alcohol, such as cetyl alcohol.

Insect repellent sticks which liquify when rubbed on the human skin are described in U.S. Pat. No. 2,819,995 (Wassell), the stick components being insoluble in water and comprising an active ingredient, fatty acid such as stearic acid, ozokerite wax and no soap, the stick being said to overcome the disadvantages of a soap-gel repellent stick comprising an active ingredient and sodium stearate. An insect repellent alcoholic soap gel stick for application to the skin area is described in U.S. Pat. No. 2,465,470 (Omohundro et el.).

U.S. Pat. No. 4,473,582 (Greene) discloses an insecticidal package for use against crawling insects, the package comprising a cylindrical tube-like receptacle containing a solid insecticidal stick composition comprising insecticide, fatty hydrocarbon monoether of propylene glycol, monoethanolamide of fatty acid, and, optionally, a lubricating agent, such as silicone oil (polysiloxane) to facilitate movement of the insecticidal stick within the receptacle. The stick is rubbed onto the surface to be treated, usually along areas where the target insects have been seen or where they may find harborage, e.g., a baseboard.

Insecticidal livestock ear tags, tail tags, pet collars, or strips, comprising an insecticide dispersed in a thermoset matrix, are described in recent U.S. Pat. No. 5,194,265 (Boettcher et al.).

A gellable slow release insecticidal composition for various animals is described in U.S. Pat. No. 4,762,718 (Marks) and it comprises a film-former, such as hydroxypropyl cellulose, and an in situ insecticide.

The present invention, in one aspect, provides a solid ectoparasite control composition, which can be in the form of a shaped article, such as a stick, that is an elongated shape, preferably cylindrical or other applicable form which is adapted to be rubbed or spread by hand, for example, from a push-up receptacle or applicator tube, on the hair coat or fur of a domesticated animal or household pet, such as a dog, cat, or horse, to transfer or deposit a thin, solid, cosmetically acceptable, substantive coating or layer of the ectoparasite control composition on the hairs of the coat of the animal, for example, its ears, back, or hindquarters, to control, for example to kill or repel, ectoparasites, such as fleas and ticks, which are on or come on the animal and are likely to cause it to be stressed, uncomfortable, or infected with disease.

The ectoparasite control composition of this invention can be made from a heated precursor liquid which is a solution or dispersion of its components or ingredients and which is gelled or solidified on cooling into a desired stick or other applicable form, which is soft and abradable but firm or hard enough to retain its shape during normal storage and use and permit an effective topical application to be rubbed on the hair coat of the animal. The components of the composition are stably and homogenously dispersed therein and comprise an ectoparasite control agent or anti-ectoparasite agent, e.g., a pyrethrum insecticide, a water-insoluble acrylate polymer, such as polymer with polymeric acrylate segment(s) with or without polysiloxane segment (s), which imparts substantivity to the applied coating of the ectoparasite control composition and thereby prolongs or extends its ectoparasite control residual activity, e.g., at least 6 days, preferably for 2 weeks or more, and, as a further essential component, a normally solid, inert, water-soluble gelling (or bodying) agent, such as sodium stearate, which gels or solidifies the precursor liquid mixture of the components, for example, after it is poured into and cooled to room temperature (e.g., 20° C.) in its dispensing receptacle (e.g., such as that used for antiperspirant or deodorant sticks), the gelling agent sustaining the stick shape or other applicable form during normal storage and use thereof e.g., at temperatures up to at least about 110° F. (43° C.).

The stick or other applicable shape can be applied to the hairy coat of the domesticated animal by rubbing or spreading the end of it on the coat, preferably in the direction of the lay of its hairs, to thereby deposit thereon, for example, on the ears, back, or hindquarters of the animal, a relatively uniformly thin, non-migratory, non-smearing, solid layer or coating of the ectoparasite control composition (without it hardening or liquefying). Magnification has shown the so-treated hairs to be discretely and uniformly coated. The applied coating is in a cosmetically acceptable form, that is, the coating has an appearance and tactibility that is not objectionable to the pet owner or animal.

The applied coating is generally transparent or translucent and may be colorless or light yellow or be of other aesthetically or cosmetically acceptable color and the coating is somewhat shiny, cohesive but not tacky or sticky or messy, and it will feel smooth (not crumbly or friable or stiff) and somewhat oily, slippery or lubricious, and the treated coat is not matted when the ectoparasite control composition is applied to deposit only the relatively uniformly thin coating necessary to provide the desired ectoparasite control. The applied coating is mycologically stable and not toxic or irritating to mucous membrane and has no objectionable odor. The coating is normally solid at the normal body and skin temperatures of the animal.

The activity of the ectoparasite control agent is effectively long due to the substantivity imparted by the polymer component, and the ectoparasite control agent does not "bleed" or "bloom" from the stick or coating thereof. As such, the normal activity of the animal, for example, its running or laying down on the ground, carpet, upholstery, etc., and the normal exposure to the elements, such as rain, will not significantly remove the applied coating or significantly lessen the effective control activity of the active ingredient, that activity lasting, for example, 6 to 14 days or more, during which the cosmetic acceptability of the coating also is not significantly lessened. The amount of ectoparasite control composition applied will be sufficient for effective control and generally will be 0.1 to 0.3 grams/kilogram of animal body weight. If needed, the application of the control composition to the animal can be repeated. If desired, the coating, though water resistant or repellent, can be removed from the hair coat by washing it with warm water and a mild detergent or shampoo, such as is normally used to maintain cleanliness of the animal.

BRIEF DESCRIPTION OF THE DRAWINGS

In the accompanying drawing, FIG. 1 is an isometric view of an embodiment of the ectoparasite control package of this invention in the form of a push-up type applicator for dispensing an ectoparasite control stick of this invention which is also shown in the isometric view of FIG. 2. FIG. 3 is a view in elevation and detail of the rotable means shown in FIG. 1.

The ectoparasite control agents which can be used as the active components or ingredients of the compositions of this invention are generally any substance (or group of substances, such as those specified by the U.S. Environmental Protection Agency, "E.P.A.") that will prevent, destroy, repel or mitigate any ectoparasites that commonly are on or infest domesticated animals with hair coats, particularly household pets or companion animals, for example, dogs and cats, such ectoparasites typically being fleas, e.g., *C. felis*, and ticks, e.g., *R. sanguineus* and *D. variabilis*. Such ectoparasite control agents, or anti-ectoparasitic agents, may be an insecticide, pheromone, insect growth regulator, or repellent, for example, those described and listed in said U.S. Pat. No. 5,194,265 (Boettcher et al.), which description and listing are incorporated herein. Also incorporated herein by reference is the description of the pyrethrum insecticide products in said Canadian Patent 1,286,985 (Matteson et al.). Generally, the classes of insecticides which can be used include known organophosphates such as chloropyrifos, synthetic and natural pyrethrins such as permethrin, and carbamates such as propoxur.

The ectoparasite control agents can be used in the practice of this invention in the form of dilute solutions in organic solvents, which may also include stabilizers and inert materials, and can be used together with their known synergists which enhance the activity of the agents. A particularly useful agent, incorporated as the active ingredient in the preferred ectoparasite control stick of this invention, is a contact pyrethrum insecticide, such as that product sold as "Kenya Pyrethrum Extract Refined Concentrate," a light amber liquid which, according to its Material Safety Data Sheet (Nov. 7, 1989), contains 54% pyrethrins, 16% isoparaffinic solvent, 5% (max.) 2,6-di-tert-butyl-4-methylphenol or "butylated hydroxytoluene" (BHT) stabilizer, and 25% inert materials, this product having a E.P.A. Registration No. 4713-5. Synergists which can be used in this invention along with pyrethrum and pyrethroid insecticides include piperonyl butoxide and others described on p. 195–197 of Chap. 10 of "Pyrethrum the Natural Insecticide," edited by J. E. Casida, Academic Press, New York (1973), which description, as well as the description of synergists in said Canadian Patent 1,286,985, are incorporated herein by reference.

The stabilizers, that is, antioxidants and ultraviolet absorbers which can be used in this invention along with the active anti-ectoparasite agent include those also described in said Canadian Patent 1,286,985, which description is also incorporated herein.

The organic solvents which can be used to prepare a solution of the active ectoparasite control agent, e.g., as a 20 to 60 wt % solution, as a component in the compositions or sticks of this invention, include those normally used in supplying commercial products of such agents, such as isoparaffins, kerosene, ethanol, acetone and ethylene dichloride.

The polymer component of the ectoparasite control composition of this invention, viz., the component which imparts substantivity to the coating applied to the animal so as to prolong the residence of the active ingredient on the hair coat of the animal, is an acrylate polymer. A class of such polymers can be represented by the general formula:

wherein:
n is an integer which represents the number of repeating units shown in parenthesis, n generally being 10 to 100,000, preferably 50 to 5000;
each $R_1$ in a repeating unit is independently a hydrogen atom or a methyl group, —$CH_3$;
each $R_2$ in a repeating unit is independently a hydrogen atom, hydrocarbon moiety (such as an alkyl group, with 1 to 20 carbon atoms, e.g., isobutyl, or a cycloalkyl group with 3 to 8 carbon atoms, e.g., cyclohexyl), an organic moiety containing a fluoroaliphatic group, for example, derived from the "A" monomers described in U.S. Pat. No. 4,972,037 (such as a N-alkyl-perfluoroalkylsulfonamidoalkylene, e.g., —$CH_2CH_2N(CH_3)SO_2C_8F_{17}$), or a poly(dialkylsiloxane) group (e.g., —$(CH_2)_3[Si(CH_3)_2O]_mSi(CH_3)_2(CH_2)_3CH_3$ wherein m is an integer which represents the number of repeating units shown in brackets, m generally being 6 to 700, perferably 60 to 300.

Another class of acrylate polymer which can be used as the substantive polymer component in the compositions or sticks of this invention is a vinyl-silicone graft or block copolymer comprising a silicone polymer segment and a vinyl polymeric segment. Such polymer can be made by a polymerization process using a mercapto-functional silicone transfer agent. The weight ratio of vinyl polymer block (segment A in formula II) to silicone segment of the copolymer can vary. The preferred copolymers are those wherein the weight ratio of vinyl polymer segment to silicone segment ranges from about 98:2 to 40:60, in order that the copolymer possess properties inherent to each of the different polymeric segments. Such copolymer can be represented by the general formula:

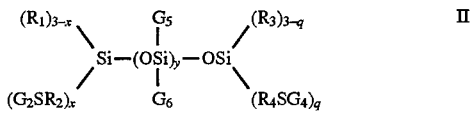

wherein $R_1$ are monovalent moieties which can independently be the same or different and are selected from the group consisting of alkyl, aryl, alkaryl, alkoxy, alkylamino, hydroxyl, hydrogen, and fluoroalkyl;

$R_2$ can independently be the same or different and are divalent linking groups;

$R_3$ are monovalent moieties which can independently be the same or different and are selected from the group consisting of alkyl, aryl, alkaryl, alkoxy, alkylamino, hydroxyl, hydrogen, and fluoroalkyl;

$R_4$ can independently be the same or different and are divalent linking groups;

x is an integer of 0–3;

y is an integer of 10 or greater;

q is an integer of at least 1;

$G_5$ are monovalent moieties which can independently be the same or different selected from the group consisting of alkyl, aryl, alkaryl, alkoxy, alkylamino, fluoroalkyl, hydrogen, and —ZSA;

A is a vinyl polymeric segment consisting essentially of polymerized free radically polymerizable monomer;

$G_6$ are monovalent moieties which can independently be the same or different selected from the group consisting of alkyl, aryl, alkaryl, alkoxy, alkylamino, fluoroalkyl, hydrogen, and —ZSA;

$G_2$ comprises A;

$G_4$ comprises A; and

Z is a divalent linking group; useful divalent linking groups include (but are not limited to) $C_1$ to $C_{10}$ alkylene, alkarylene, arylene and alkoxyalkylene.

The above-described acrylate polymers include those described in the literature, for example, U.S. Pat. Nos. 4,172,122 (Kubik et al.), 4,972,037 (Garbe et al.), 4,981,903 (Garbe), 5,032,460 (Kantner et al.), 5,194,265 (Boettcher) and Can. Pat. No. 1,286,985 (Matteson etl al.), which descriptions are incorporated herein by reference. Some examples of such polymers are poly(isobutyl methacrylate-co-N-methyl perfluorooctylsulfonamidoethylacrylate)-g-poly(dimethylsiloxane) and poly(dimethylsiloxane)-g-poly(isobutyl methacrylate), such as those described as SA 70-5 IBMMF and VS 70 IBM in commercial bulletin 70-0705-2562-4 of the Minnesota Mining and Manufacturing Company; and poly(isooctyl acrylate-co-stearyl methacrylate-co-acrylic acid). These polymers may be used, in the formulation of the compositions or sticks of this invention, as solutions in the solvents used in their polymerization preparation or in other solvents such as aliphatic, aromatic, or oxygen-containing polar solvents, e.g., alcohols, ketones, esters, glycols, silicones, and ethers, examples of such solvents being propylene glycol and fatty alkyl esters of benzoic acid. Mixtures of these solvents can be used and the solvents can also be used to solubilize the ectoparasite control agent and synergist adjuvant therefor.

The gelling or bodying components typically will provide ectoparasite control compositions of this invention that generally have melting points greater than 110° F. (43° C.). Such gelling or bodying components have low or no odor, and are preferably those which are soluble or dispersible in water and the hot precursor liquid, and which can also be incorporated in the compositions as a diluent. Substances which can be used to gel the precursor liquid and to sustain the shaped forms or sticks made therefrom, representively are sodium stearate, the preferred gelling agent, and various other compatible gelling agents which can be readily dissolved in and mixed with the precursor liquid.

To facilitate the homogeneity of the water component with the oil or organic components, particularly the ectoparasite control agents, which are active ingredients in the compositions of this invention, the substantive polymer, and the organic solvents used to form the solutions thereof in formulating the ectoparasite control composition, suitable surfactants can be used, such as those non-ionic surfactants that will aid in preparing the precursor liquid mixture as a water-in-oil emulsion. Alkoxylated fatty alcohols, such as polyoxypropylene polyoxyethylene cetyl ether, are particularly useful for emulsifying water into the oily components of the ectoparasite control composition. Generally, the amount of surfactant to be used will be 15 to 45 wt %, preferably 18 to 35, wt %, and the amount of water emulsified will be 15 to 30 wt %.

Other optional components which can be incorporated in the precursor liquid mixture are those which will enhance application (rubbing or spreading) of the stick and/or which will enhance the cosmetic acceptability of the applied coating. Lubricity agents such as silicone fluids are such optional components for imparting lubricity to the applied coating.

The relative amounts of the various components of the ectoparasite control compositions of this invention can vary and the particular amount of each will be that amount which is sufficient or best for it to perform its function. In the case of the ectoparasite control agent, the amount of this component generally will be that amount which will provide the desired killing, prevention, repelling, or mitigation of the target ectoparasite over the desired duration. The amount of the polymer component to be used in the ectoparasite control composition will be that amount generally sufficient to impart the desired substantivity to the applied coating, that is, the desired period of effective ectoparasite control, e.g., 14 or more days after application of the stick to the hair coat of the animal to be treated. The amount of gelling agent to be used will be that sufficient to solidify the precursor liquid upon molding and cooling it to form the desired shape or stick thereof and sustain it in that form during its storage and application to the animal for its intended ectoparasite control. Table 1 sets forth ranges of amounts of essential and optional components that generally can be used in preparing the ectoparasite control compositions and desired shapes or sticks thereof according to this invention.

TABLE 1

| Component* | Amount, wt % |
| --- | --- |
| Ectoparasite control agent | 0.05 to 20, preferably 0.5 to 5 |
| Synergist | 0 to 16 |
| Substantive acrylate polymer | 0.05 to 5 |
| Lubricity agent | 0 to 10 |
| Organic solvent | 15 to 45 |
| Water | 15 to 30 |
| Surfactant | 15 to 45 |
| Gelling agent | 2 to 10 |

*Each of the listed components can actually be mixtures of several like components, e.g., the listed "Organic solvent" can represent the solvent in which the ectoparasite control agent is dissolved and formulated and the solvent in which the substantive polymer is dissolved and formulated.

In preferred embodiments of this invention, the ectoparasite control agent comprises pyrethrin insecticide as the active ingredient, the substantive polymer is poly(isobutyl methacrylate-co-N-methyl-perfluorooctylsulfonamidoethyl acrylate)-g-poly(dimethylsiloxane) and sodium stearate is the gelling agent. Table 2 sets forth the various components and ranges of amounts thereof which can be used to prepare ectoparasite control compositions (and sticks or other forms thereof).

TABLE 2

| Component | Amount, wt % |
| --- | --- |
| Pyrethrin insecticide, 54 wt % solution in kerosene | 0.05 to 4, preferably 0.5 to 3 |
| Piperonyl butoxide synergist | 0 to 15, preferably 2.2 to 13 |
| Poly(isobutyl methacrylate-co-N-methyl-perfluorooctylsulfonamido-ethyl acrylate) -g-poly(dimethylsiloxane) substantive polymer, 25 wt % solution in Finsolv TN | 0.05 to 20, preferably 0.5 to 8 |
| Poly(dimethylsiloxane)cyclic tetramer lubricity agent | 0 to 5, preferably 2 to 5 |
| $C_{12}$-$C_{15}$ alkyl benzoate solvent for substantive polymer | 5 to 10, preferably 7 to 10 |
| Propylene glycol | 20 to 30, preferably 22 to 26 |
| Polyoxypropylene (5) Polyoxyethylene (20) Cetyl ether (surfactant) | 15 to 50, preferably 20 to 25 |
| Water | 15 to 30 preferably 18 to 25 |
| Sodium stearate | 2 to 10 preferably 3 to 6 |

The ectoparasite control compositions of this invention can be made by heating for example, to 50° to 90° C., preferably about 70° C., while stirring a precursor mixture of the solvent solution of the substantive polymer, surfactant, and water, thereby forming a water-in-oil emulsion or dispersion, then, while the latter is still hot, adding thereto the gelling agent (in a particulate form, e.g., powder) while stirring to dissolve it, cooling the resulting liquid mixture for example, to 50° to 70° C., preferably to about 60° C., then, while stirring the cooled mixture, adding thereto the ectoparasite control agent (typically as a concentrate in a solvent) and, if used, the synergist and the silicone fluid components. The final resulting mixture can then be poured into suitable stick molds and allowed to cool to ambient room temperature (e.g., 20° C.), during which cooling the composition will solidify in the desired shape or form. (Alternatively, the precursor liquid mixture can be cooled to solidify it in other solid forms, e.g., pellets or bars, which can be stored and shipped and later heated to form a liquid that can be poured into a mold and cooled to form the stick.)

Push-up type applicators or packages can be used to mold the sticks and dispense the coating therefrom when the sticks are applied to the hair coat of the animal to be treated therewith to control ectoparasites thereon. Push-up applicators of this type are described in the art, for example, in U.S. Pat. Nos. 2,818,167 (McKinley), 3,826,232 (Duffey), and 4,473,582 (Greene), which descriptions are incorporated herein.

The accompanying drawing illustrates an embodiment of an ectoparasite control package which can be used to provide control compositions of this invention generally designated by reference number 10. It comprises a tubular or cylindrical body or casing 11, which is preferably made of molded thermoplastic, such as polyethylene, having an oval cross-section and an internal chamber 12 defined by the inner surface or wall of the tubular body. The tubular body 11 has an open end 13 and a removable member 14 press-fitted in the other open end. The open end 13 can be closed by press-fitting into it a closure member 16. A removable cap 17, likewise oval in cross-section, is adapted to be press-fitted over a tapered portion 18 of the tubular body 11 to enclose the open end 13 with (or without) the member 16 in place. Disposed within the chamber 12 is the ectoparasite control stick 20, which is likewise cylindrical and oval in cross-section but can be slightly smaller in that respect so that it can be slid easily in and out of the chamber, the length of the stick, as initially molded, being somewhat shorter than the length of the chamber.

The removable member 14, shown in detail in FIG. 3, comprises a cap 21, which likewise is oval in cross-section and press-fitted within the end of the chamber 12, and it has a suitable journal 22, in which a rotable, threaded stem 24 is axially mounted and adapted to axially pass through a piston 26 which is likewise oval in cross-section and adapted to slide back and forth within chamber 12 of the tubular body 11. The stem 24 is affixed on one end to a knob 27 whose outer surface can be knurled as shown and rotated by hand (viz, by the thumb and forefinger), the tubular body 11 having opposite-disposed cut-out portions 28 to provide access to the knob for the purpose of such hand Operation, which can push the stick 20 in or out of chamber 12 when closure member 16 and cap 17 have been removed.

To expose the stick 20 for application to the hair coat of the animal to be treated therewith, cap 17 and closure member 16 are removed and the knob 27 is rotated in a clock-wise manner to push the stick out the open end 13 sufficiently to expose the adjacent free end of the stick so that, by then grasping the tubular body 11 by hand, the exposed end of the stick can be rubbed on the hair coat for purposes of applying thereto a coating of the ectoparasite control composition for control purposes. After application of the coating, knob 27 can be rotated in the opposite manner to retract stick 20 back into chamber 12, and closure member 16 and cap 17 can be replaced to protect the stick from damage.

In preparing the applicator 10, the stick precursor liquid can be poured into chamber 12 of the empty tubular body 11 when it is in a vertical position with its end closure member 16 (and cap 17, if desired) in place, and with the member 14 and piston 26 removed, the precursor mixture being poured through the end of the tubular body in which the member 14 is normally fitted. After filling the chamber 12 with the requisite amount (e.g., about 2.5 ounces) of the precursor liquid, the assembly of the member 14 and piston 26 can be inserted in position within chamber 12, the piston having been retracted on stem 24 to accommodate the poured volume of the precursor liquid. Upon standing and cooling, the precursor liquid gels or solidifies in situ to form the stick 20, which stick fits and is easily movable within chamber 12 as described above. Piston 27 can have one or more holes 29 provided in it to allow for escape of air when the assembly of member 14 and piston 26 is positioned as described. An inner integral ring 30 on the inner wall of tubular body 11 acts as a stop means to limit the retractable extent of piston 26.

A specific ectoparasite control composition (and stick) of the invention was made up of the components, and amounts thereof, set forth in Table 3.

TABLE 3

| Component | Amount, g |
|---|---|
| Poly(isobutyl methacrylate-co-N-methyl-perfluorooctylsulfonamido-ethyl acrylate) -g-poly(dimethylsiloxane) substantive polymer, 25 wt % solution in Finsolv TN | 33.4 |
| $C_{12-15}$-alkyl benzoate[1] | 46.3 |
| Polyoxypropylene polyoxyethylene cetyl ether[2] | 193.3 |
| Propylene glycol | 193.3 |
| Deionized water | 160.8 |
| Sodium stearate | 32.2 |
| Pyrethrins insecticide concentrate[3] | 26.7 |
| Piperonyl butoxide | 114.2 |
| Poly(dimethylsiloxane)cyclic tetramer[4] | 33.3 |

[1]Finsolv ™ TN solvent
[2]Procetyl ™ AWS surfactant
[3]"Kenya Pyrethrum Extract Refined Concentrate"
[4]"VS-7207" silicone product of Union Carbide Corp.

The substantive polymer component listed first in Table 3 was prepared by polymerization of 10,000 molecular weight methacryloxypropyl terminated polydimethylsiloxane macromonomer (PDMS) with 2-(N-methyl perfluorooctylsulfonamido) ethyl acrylate (MeFOSEA) and isobutyl methacrylate (IBM). Briefly, a mixture of 25 parts of PDMS (Mw=10,000), 5 parts of MeFOSEA, and 70 parts of IBM in 135 parts of ethyl acetate and 15 parts of isopropyl alcohol was added 0.25 parts of 2,2'-azobisisobutyronitrile (AIBN). This solution was purged with nitrogen and sealed in a bottle under nitrogen atomosphere. The bottle was heated in an Atlas Launder-O-Meter® (like a water bath) at 60° C. for 24 hours. To 50 gram of the reaction mixture prepared above, 60 gram of Finsolv™ TN was charged. Ethyl acetate and isopropanol were removed on a rotary evaporator to give 80 gram (25 wt % polymer) of a very viscous polymer solution in Finsolv™ TN.

In preparing the formulation of Table 3, the mixture of the first five listed components was heated to 70° C. while stirring the mixture in a 1000 ml beaker at 300–350 rpm. The sodium stearate was added to the mixture and stirred therewith until it dissolved. The mixture was then cooled to 60° C. while stirring. The pyrethrins insecticide concentrate, piperonyl butoxide, and silicone component were then added and the resulting final precursor liquid was cooled to 55° C. and poured into ten stick applicators like that illustrated in the drawing (show as Item No. 9404 in the catalog, copyright 1988, of W. Braun Co.), the so-poured liquid solidifying in stick form (each stick being about 2.5 oz. and about 3¼-inch long and ¾ inch wide) in each of the applicators upon standing at room temperature.

(Other sticks of this invention were made as described above from formulations similar to that of Table 3 but using different anti-ectoparasite agents, namely, "Permanone 80" synthetic pyrethroid, "Dursban" organophosphate, "Sendran" carbamate, "DEET" repellant, and "Nylar" insect growth regulator.)

The sticks prepared with the composition of Table 3 were clinically evaluated for effectiveness against fleas and ticks on dogs infested with such pests. The sticks were applied to the hair coat of the animals to provide 0.34 to 0.39 g/kg body weight. Against the fleas, the sticks provide a 91% to 96% reduction of fleas through Day 13 post treatment regardless of whether the sticks were applied to the dogs "with" the lay of the hair (Method A) or "against" the lay of the hair (Method B). The sticks also provided 81% to 84% reduction of fleas through Day 16 post treatment regardless of which Method A or B was used. The sticks at 20 days post treatment provided a 78% reduction of fleas when the sticks were applied by Method A and a 58% reduction of fleas when the sticks were applied by Method B. Thus, the data show the ectoparasite control composition of this invention was effective against fleas, the coating on the dogs having a residual effect over a prolonged period, which was attributed to the substantivity of the coating imparted thereto by the acrylate polymer component. This effectiveness of the sticks was superior to a comparable stick formulation that omitted the acrylate polymer, in that the sticks of this invention extended the residual effectiveness by 7 days over the comparable sticks formulated without the substantive acrylate polymer.

In the clinical tick evaluations, the sticks made from the formulation of Table 3 provided 85%, 67% and 29% reduction of ticks (R. sanguineus) through Days 6, 13, and 20, respectively, post treatment when the sticks were applied by Method A. When the sticks were applied by Method B, the reduction of ticks was 29%, 69% and 60% through Days 6, 16, and 20, respectively, post treatment. When compared again with the results obtained with sticks made from a comparable formulation that omitted the acrylate polymer, these data show in general that the sticks of this invention (Table 3 formulation) extended the residual effectiveness against R. sanguineus by 7 to 8 days (from 13 days to 20 days) over the comparable sticks formulated without the substantive acrylate polymer.

The sticks with the formulation of Table 3 were also clinically evaluated against adult D. variabilis on dogs and found to be effective for ectoparasite control, the data of such evaluation showing residual effectiveness at or near the 85% level through 6 days post treatment using Method B and superior in that respect to the results obtained with the comparable sticks whose formulation omitted the substantive acrylate polymer.

In carrying out the clinical evaluations described above, the animals remained healthy, did not appear stressed or uncomfortable, and showed no reaction atypical to the animal's behavior that could be deemed related to the presence of the stick coating.

Table 4 sets forth the formulation of three other ectoparasite control compositions of this invention that were prepared in stick form similarly to the sticks prepared from the formulation of Table 3.

TABLE 4

| Components | Formulations | | |
|---|---|---|---|
| | A | B | C |
| Copolymer of 35 wt % isooctyl acrylate, 45 wt % stearyl methacrylate, and 20 wt % acrylic acid, as a 30 wt % solution in Finsolv TN | 2.34 g | 1.99 g | 1.82 g |
| $C_{12-15}$ alkyl benzoate (Finsolv TN) | 3.90 | 4.30 | 4.95 |
| Polyoxypropylene (5) polyoxyethylene (20) cetyl ether* | 15.06 | 12.84 | 12.73 |
| Propylene glycol | 15.01 | 12.72 | 12.86 |
| Deionized water | 12.49 | 10.63 | 10.61 |
| Sodium Stearate | 2.50 | 2.00 | 2.00 |
| Insecticide: | | | |
| "Kenya Pyrethrum Extract Refined Concentrate" | 2.19 | | |
| "Permanone 80" synthetic pyrethroid | | 3.09 | |
| "Dursban" chlorpyrifos, 99% | | | 2.40 |
| Piperonyl butoxide, 80% | 9.08 | — | — |
| Poly(dimethylsiloxane)cyclic tetramer** | 0.69 | 0.62 | 0.68 |

*"Procetyl AWS" product of Croda Inc.
**"VS-7207" Silicone product of Union Carbide Corp.

Various modifications and alterations of this invention will become apparent to those skilled in the art without departing from the scope and spirit of this invention.

What is claimed is:

1. A solid ectoparasite control composition for use on an animal's coat comprising 1) about 0.05–20 wt. % pyrethrin insecticide;
2) about 16 wt. % piperonyl butoxide;
3) about 0.5–5 wt. % poly(isobutyl methacrylate-co-N-methyl perfluorooctylsulfonamidoethyl acrylate)-g-poly(dimethylsiloxane);
4) about 2–10 wt. % sodium stearate;
5) about 15–45 wt. % polyoxypropylene polyoxyethylene cetyl ether;
6) about 15–35 wt. % $C_{12-15}$ alkylbenzoate and propylene glycol; and
7) about 10 wt. % poly(dimethylsiloxane)cyclic tetramer; and
8) about 15–30 wt. % water, wherein the solid ectoparasite control composition is adapted to be rubbed or spread by hand on an animal's coat to transfer or deposit a thin, solid, cosmetically acceptable, substantive coating on the animal's coat to kill or repel ectoparasites which are on or come on the animal.

2. The solid ectoparasite control composition of claim 1 in the form of a shaped stick adapted to be dispensed from a tubular receptacle.

3. The solid ectoparasite control composition of claim 1 in the form of a shaped stick which is adapted to be rubbed or spread by hand from a push-up receptacle tube on an animal's coat.

4. A method of treating an animal's coat to control ectoparasites which are on or come on the animal comprising the step of applying a solid ectoparasite composition of claim 1 on the coat of the animal.

* * * * *